United States Patent [19]

Sisto et al.

[11] Patent Number: 5,013,723
[45] Date of Patent: May 7, 1991

[54] NEW THYMOPENTIN RETRO-INVERSO ANALOGS AND FRAGMENTS THEREOF, A PROCESS OF PREPARATION OF THE NEW COMPOUNDS AND THE INTERMEDIATES OBTAINED THEREIN

[75] Inventors: Alessandro Sisto, Rome; Antonio Verdini, Monterotondo, both of Italy

[73] Assignees: Eniricerche S.p.A., Milan; Sclavo S.p.A., Siena, both of Italy

[21] Appl. No.: 168,237

[22] Filed: Mar. 15, 1988

[30] Foreign Application Priority Data

Mar. 19, 1987 [IT] Italy ............................. 19763 A/87

[51] Int. Cl.$^5$ .................... A61K 37/02; C07C 229/24; C07C 251/02
[52] U.S. Cl. ........................................ 514/19; 514/18; 530/330; 530/331; 560/169; 562/560
[58] Field of Search .......................... 562/560; 514/19; 560/169

[56] References Cited

U.S. PATENT DOCUMENTS 4,505,853  3/1985  Goldstein et al. .................. 530/330
4,547,489  10/1985  Goldstein et al. .................. 530/330
4,629,723  12/1986  Goldstein et al. .................. 530/330

FOREIGN PATENT DOCUMENTS 0269389  6/1988  European Pat. Off. ............. 514/19

OTHER PUBLICATIONS

*Archives of Biochemistry*, vol. 242, No. 1, pp. 248–255, Oct. 1985, "Structural Requirements for the Biological Activity of Thymopentin Analogs".

Primary Examiner—Glennon H. Hollrah
Attorney, Agent, or Firm—Oblon, Spivak, McClelland, Maier & Neustadt

[57] ABSTRACT

New retro-inverso analogs of thymopentin (TP5) and of its tripeptide fragment (TP5$^{1-3}$) of general formula (I)

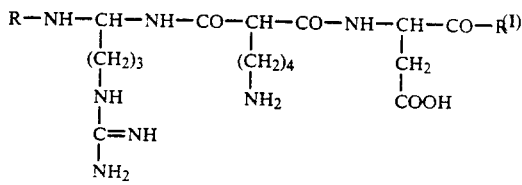

are described wherein R is hydrogen or an acyl radical, and R$^1$ is —OR$^2$ or

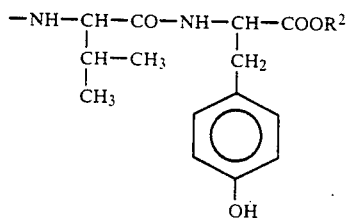

wherein R$^2$ is hydrogen or a hydrocarbyl radical, and the corresponding pharmaceutically acceptable acid- or base-addition salts.

The new compounds are enzyme-resistant immunomodulatory peptides.

5 Claims, No Drawings

NEW THYMOPENTIN RETRO-INVERSO ANALOGS AND FRAGMENTS THEREOF, A PROCESS OF PREPARATION OF THE NEW COMPOUNDS AND THE INTERMEDIATES OBTAINED THEREIN

The present invention refers to new thymopentin retro-inverso analogs and fragments thereof, a process of preparation of the new compounds, the intermediates obtained therein and the use of the new compounds for the preparation of pharmaceutical compositions.

A first object of the present invention are the retro-inverso analogs of thymopentin (TP5) and of its tripeptide fragment (TP5$^{1-3}$), having the following general formula

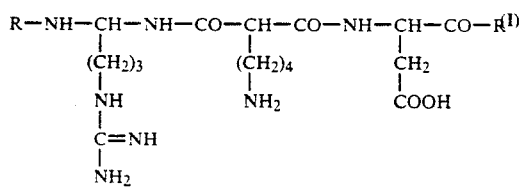

wherein
R is hydrogen or an acyl radical, and
R$^1$ is an —OR$^2$ or a

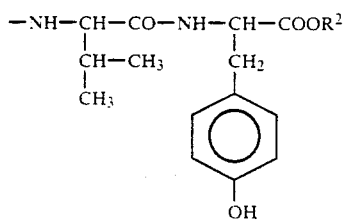

group wherein R$^2$ is hydrogen or a straight or branched alkyl radical of from 1 to 6 carbon atoms, a straight or branched alkenyl or alkynyl radical of from 3 to 6 carbon atoms, or an aryl-alkyl or alkyl-aryl radical of from 7 to 12 carbon atoms,
and the corresponding pharmaceutically acceptable acid- or base-addition salts.

The new compounds of the present invention which are indicated above by their structural formula, can be identified more concisely, using the internationally recognized peptide symbology, as :

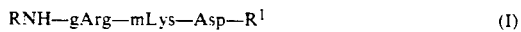

wherein R is hydrogen or an acyl radical, and
R$^1$ is an —OR$^2$ or a —Val—Tyr—OR$^2$ group wherein
R$^2$ is as defined above.

In the above formula gArg represents a geminal diamino residue derived from arginine by replacing the terminal carboxyl group with an amino group, while mLys designates a malonyl residue substituted at the 2-position with the lysine side-chain. Asp, Val, and Tyr represent the aspartic acid, valine and tyrosine residues respectively. For the purposes of the present invention the term "acyl radical" identifies acyl radicals derived from straight or branched alkanoic acids containing from 1 to 6 carbon atoms such as, for instance, formyl, acetyl, propionyl, succinoyl, and the like, and from benzoic and substituted benzoic acids, such as for instance benzoyl, 4-nitro-benzoyl, 2,3,4-trimethoxybenzoyl, etc..

As employed herein, the phrase "pharmaceutically acceptable salts" refers to acid- or base-addition salts of the new compounds of formula (I), the anions or cations of which are relatively non-toxic and innocuous to mammals at dosages consistent with good biological activity so that side effects ascribable to said anions or cations do not vitiate the beneficial effects of the active compounds. As acids which are able to form pharmaceutically acceptable addition salts with these peptides, there may be mentioned inorganic acids such as hydrochloric acid, hydrobromic acid, phosphoric acid, sulfuric acid, and the like, organic carboxylic acids, such as formic acid, acetic acid, propionic acid, lactic acid, malonic acid, succinic acid, benzoic acid, etc. and organic sulfonic acids such as methanesulfonic acid or naphthalenesulfonic acid or the like.

As bases which are able to form pharmaceutically acceptable salts with the compounds of formula (I) are included inorganic bases such as sodium hydroxide, potassium hydroxide, ammonium hydroxide, and the like, and organic bases such as for instance triethylamine, triethanolamine, and the like. Said addition salts can be obtained either directly from the process of this invention for the preparation of the new retro-inverso peptides or by reacting the peptide of formula (I) with one or more equivalents of the appropriate acid or base, according to conventional methods. If desired, a particular acid addition salt is converted into another acid addition salt by treatment with the appropriate ion exchange resin in the manner described by R. A. Boissonas e al. in Helv.Chim.Acta, 43, 1349, (1960). Suitable ion exchange resins are cellulose based cation exchangers and strongly basic anion exchange resins. A preferred group of compounds of the present invention comprises those compounds of formula (I) wherein R$^1$ is as defined above, R$^2$ is hydrogen, and R represents a hydrogen atom or a metabolically labile acyl radical i.e. an acyl radical which is easily and quickly cleaved in vivo during the preliminary stages of the metabolic fate of the product and does not show any toxic or contraindicated effects in therapy, at the concentration which provides for the desired pharmacological effect of the biologically active compound of formula (I).

A most preferred group of compounds comprises those compounds of formula (I) wherein R represents a hydrogen atom, R$^1$ is as defined above and R$^2$ is hydrogen.

The compounds of the present invention have remarkable immunopharmacological properties. In the last fifteen years, G. Goldstein and his co-workers have investigated the biological activity and possible pharmacological role of a polypeptide hormone secreted by the epithelial cells of the thymus, thymopoietin (G. Goldstein, Nature, 247. 11, (1974); D. H. Schlesinger et al., Cell, 5. 361, (1975); T. Audhya et al., Biochemistry, 20, 6195, (1981)), whose primary sequence contains 49 amino acids.

Thymopoietin has a number of biologic regulatory effects, affecting neuromuscular transmission (G. Goldstein, Lancet, 2, 119, (1968)), T and B cells differentiation (M. P. Scheid et al., J.Exp.Med., 147, 1727, (1978)), and immune response (C. Y. Lau et al., J.Immunol., 125, 1634, (1980)).

Structure-activity studies have shown that the entire 49 amino acid sequence of thymopoietin is not required for biological activity, as the pentapeptide H-Arg-Lys- Asp-Val-Tyr-OH (Thymopentin -TP5) corresponding to amino acids 32 to 36 of thymopoietin, was shown to have the biological properties of the natural hormone both in vitro and in vivo (G. Goldstein et al., Science, 204, 1309, (1979)).

More particularly, in fact, in vitro experiments showed that both thymopoietin and thymopentin (TP5) selectively induce early differentiation of T lymphocytes, while inhibiting B lymphocytes maturation.

Additional in vivo studies showed that thymopentin also drove T cell differentiation in vivo in nude mice that congenitally lack a thymus and have therefore a reduced amount of circulating mature T lymphocyte (G. E. Ranges et al., J.Exp.Med., 156, 1057, (1982)), thus establishing a major immunological function of this compound. Thymopoietin and thymopentin also showed an immunoregulatory action probably due to a distinct cyclic-GMP-mediated action on peripheral T cells. More particularly, animal tests showed that thymopentin has an immunonormalizing activity in immune disbalances, in that it can bring the immune system towards normal whether it is up- or down-regulated, i.e. whether it is hyperresponsive, as in the autoimmune diseases, or it is hyporesponsive, as an example due to thymectomy or the involution of the thymus that occurs with age (E. H. Goldberg et al., Immunogenetics, 13, 201, (1981); C. Y. Lau et al., Cell Immunol., 66, 217, (1982)).

Thymopentin has been and is being used in clinical trials for the treatment of autoimmune diseases, such as rheumatoid arthritis, as well as for the treatment of primary immune deficits, caused by absence or incomplete development of thymus and consequent alteration in T lymphocytes maturation, and acute and recurrent viroses, and as an adjuvant in vaccination.

The setting up of a suitable treatment schedule is however crucial because of the difficulties in determining the effective dosage, and the appropriate route and mode of administration. It has been shown in fact that the pharmacological effect may vary significantly depending on the administration route and mode (T. Audhya et al., Surv.Immunol.Res. 4 suppl. 1, 17, (1985); and T. Audhya et al., Int.J.Peptide Protein Res., 22, 568, (1983)).

A very interesting observation is that reported by Bolla et al. in Int.J.Clin.Pharm.Res., IV(6), 431, (1984), according to which stimulation of antibodies production induced by TP5 subcutaneous treatment is completely suppressed when an equal dose is administered intravenously. A possible reason thereof is the short plasma half-life of TP5. TP5 in fact suffers from very rapid enzymatic breakdown in vivo as it is rapidly cleaved by proteases present in human plasma. It has been determined that the half-life of thymopentin in serum is approximately 1.5 minute (T. P. Tischio et al., Int.J.Peptide Protein Res., 14, 479, (1979)). A thorough research activity has been developed over the last few years aimed at obtaining TP5 analogs with an increased resistance to enzymatic degradation. See for instance EP-A-135,722 and U.S. Pat. No. 4,505,853 concerning synthetic analogs of thymopentin with variations at each of the five positions.

Recently it has been shown (L. Kisfaludy et al., Hoppe-Seylers's Z.Physiol.Chem., 364, 933, (1983)) that also thymopentin fragment 1 to 3, i.e. H—Arg—Lys—Asp—OH (TP5$^{1-3}$, has immunostimulating activity. In preliminary in vivo tests, it proved to be able to restore the immune response in thymectomized mice.

Also in this case, however, the high susceptibility of this compound to enzymatic degradation by plasma proteases and its short half-life represent remarkable disadvantages.

It has now been found that the compounds of formula (I) of the present invention simultaneously possess equivalent or enhanced biological activity and substantially increased resistance to enzymatic degradation, when compared to the corresponding parent compounds TP5 and TP5$^{1-3}$. In particular, susceptibility to enzymatic hydrolysis in human plasma of both TP5 and [gArg$^1$,(R,S)mLys$^2$]TP5, has been evaluated using heparinized human plasma and separately incubating the above peptides at a concentration of about 30 nmol/ml of plasma. Incubations are carried out at 37° C., and aliquots (100 $\mu$; each) were collected at time intervals, blocked by treatment with 10% trifluoroacetic acid and centrifuged (10,000 rpm) for 5'. Aliquots from the supernatant were assayed by chromatography and the concentration of the test peptide at the different times was measured. From the thus obtained kinetics, the half-life, i.e. the incubation time at 37° C. needed for degrading 50% of the test peptide, was calculated and is reported in following Table I

TABLE I

| Stability to enzymatic hydrolysis in human plasma | |
|---|---|
| | t$_{\frac{1}{2}}$(min.) |
| TP5 | 1.5 |
| [gArg$^1$,(R,S)mLys$^2$]TP5 | 32 |

Also the compound of formula (I) wherein R$^1$ is a group —OR$^2$ wherein R$^2$ is hydrogen, showed to have a much higher stability to plasma proteases than the corresponding parent compound TP5$^{1-3}$, with a half-life which is ten times higher.

This substantially increased stability of the retro-inverso analogs over the corresponding parent compounds TP5 and TP5$^{(1-3)}$ has been evidenced also against isolated enzymes (leucine aminopeptidase and carboxypeptidase).

The immunopotentiating activity of [gArg$^1$,(R,S)mLys$^2$]TP5 has been tested in comparison with TP5, both in vitro and in vivo, while the activity of the compound of formula (I) wherein R is hydrogen, R$^1$ is —OR$^2$ wherein R$^2$ is hydrogen, has been evaluated in comparison with the corresponding parent compound TP5$^{1-3}$, directly in vivo.

In particular, as the in vitro test, the Rosette E formation test has been performed both on peripheral blood mast cells (PBMC) and on cord blood cells (CBC). The CBC used give a percentage of Rosette E formation with sheep red blood cells (SRBC) of 20-40%. The test is based on the capability of human T cells of forming Rosette E with SRBC. The assay which has been carried out according to the metodology described by O. G. Bier at al. in Fundamentals of Immunology - Springer-Verlag (1981), consists in the incubation of CBC, with or without the test peptides, overnight at 37° C. in the presence of 5% CO$_2$. The obtained results are reported in following Table II

TABLE II

| Compound | % of live cells after incubation | % formation of Rosette E |
|---|---|---|
| CBC-blank | 100 | 23 |
| TP5 10 ng/ml | 65 | 28 |
| TP5 100 ng/ml | 65 | 33 |

TABLE II-continued

| Compound | % of live cells after incubation | % formation of Rosette E |
|---|---|---|
| TP5-RI$_{1-2}$ 10 ng/ml | 68 | 34 |

As the in vivo test, the so-called "plaque forming cells" test described by N. Jerne (same reference as above), has been used. The test is carried out incubating spleen cells of mice who had received the test peptides, with SRBC and counting the number of plaques formed. In the actual practice, groups of 3 mice each, received about 1 ng/mouse of test peptide i.p. one hour after the antigen (SRBC) inoculation. Four days after this treatment, the spleen cells are removed and the test is immediately carried out. The results are reported in following Table III

TABLE III

| Compound | Number of plaques formed | Log Number of plaques |
|---|---|---|
| Blank | 42.000 | 4.62 |
| TP5 | 48.375 | 4.68 |
| TP5-RI$_{1-2}$ | 85.583 | 4.93 |
| TP5$^{(1-3)}$ | 48.917 | 4.67 |
| TP5$^{(1-3)}$-RI$_{1-2}$ | 63.125 | 4.78 |

In Table III, as well as elsewhere throughout this patent application, "RI" means "retro-inverso". TP5-RI$_{1-2}$ thus identifies the thymopentin analog retro-inverted at the 1-2 peptide bond. TP5$^{(1-3)}$-RI$_{1-2}$ thus refers to the thymopentin tripeptide fragment TP5$^{(1-3)}$ analog retro-inverted at the 1-2 peptide bond. The "plaque forming cells" test has been repeated also by treating the test mice with TP5 or with the corresponding retro-inverso analog TP5-RI$_{1-2}$, three days before antigen (SRBC) injection.

The obtained results are reported in following Table IV

TABLE IV

| Compound | Number of plaques formed | Log Number of plaques |
|---|---|---|
| Blank | 44.000 | 4.64 |
| TP5 | 62.000 | 4.79 |
| TP5-RI$_{1-2}$ | 103.000 | 5.01 |

It is apparent in view of the above results that the peptides of the present invention are capable of affecting the immune response of the body, typically stimulating it when defective. The compounds of the present invention are therefore therapeutically useful in the treatment of various diseases caused by an immunogenic deficit. Among these diseases there can be mentioned for instance the DiGeorge syndrome, characterized by a congenital absence of thymus or the chronic or long-lasting viral, fungal, or mycoplasmatic infections.

Some of the compounds of the present invention have also an immunoregulating activity which is expressed by depressing the immune system activity when abnormal. Said compounds, including TP5-RI$_{1-2}$, are expected to have a broader therapeutical application, as immunomodulators.

A further object of the present invention are therefore the pharmaceutical compositions containing a therapeutically effective amount of one or more of the compounds of formula (I).

For the use as immunostimulators or immunomodulators, the compounds of the present invention may conveniently be administered parenterally, orally, intranasally or sub-lingually. The formulations which contain the new compounds can be prepared according to known techniques, by compounding the active principle with an inert pharmaceutical carrier and optionally with suitably selected conventional additives known to be useful in the preparation of the particular type of composition desired. Suitable pharmaceutical carriers and formulation techniques are found in standard texts, such as Remington's Pharmaceutical Sciences, Mack Publishing Co., Easton, Pa. For oral or sub-lingual administration, however, the compounds of the present invention may be administered as tablets, capsules, drops, elixirs, and the like, prepared by using the conventional carriers/additives such as starch, sugars, water, alcohol, and the like additives and optionally containing flavours, stabilisers, preservatives, and lubricating agents, etc.. For parenteral or intra-nasal use, the vehicle of choice is steril water for injections. Additives may be added according to the known techniques.

Altough the therapeutically effective daily dosage will vary from patient to patient depending upon the nature and severity of the disease, the patient's weight and age, the administration route, and other factors which those skilled in the art will recognize, the daily dosage range will generally be about 10 and 200 ng/Kg body weight which can be administered in single or multiple doses. The pharmaceutical preparations of the present invention therefore will contain the compounds of formula (I) in amount suitable to provide a daily dosage within the above indicated range.

The compounds of the present invention are conveniently prepared by condensing a peptide fragment of formula (II)

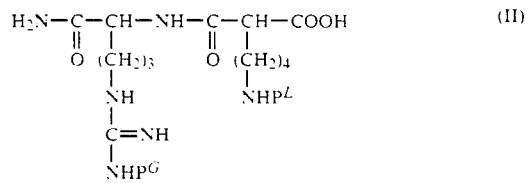

wherein
P$^L$ represents a protective group of the side-chain amino function, and
P$^G$ is a suitable protecting group of the guanidino function,
with a peptide fragment of formula (III)

wherein
R$^3$ may represent a group —OR$^2$ wherein R$^2$ is as defined above, a group —OP wherein P is a carboxyl protecting group, or a grouping of formula

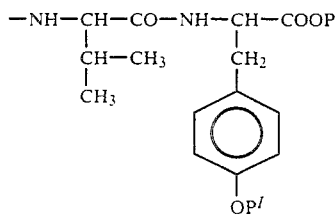

wherein

P is as defined above, and $P^I$ is a protective group of tyrosine hydroxyl function, followed by conversion of the terminal amide group of the thus obtained intermediate of formula (V)

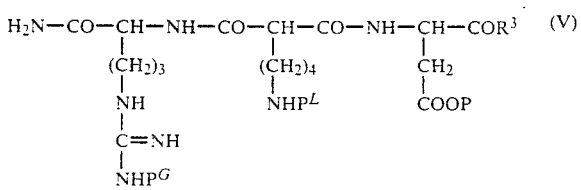

into primary amino group by treatment with I,I-bis-trifluororacetoxy-iodobenzene (TIB) to afford the intermediate of formula (VI)

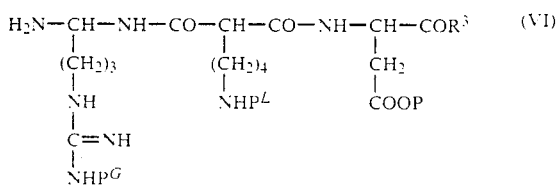

followed by the optional acylation of the terminal amino function and removal of the protecting groups. When a compound of formula (I) is desired wherein R is hydrogen and $R^1$ is an $-OR^2$ group, the sequential arrangement of the amide/amine conversion and deprotection steps may conveniently be reverted. This is unfeasible however when a compound of formula (I) is desired wherein $R^1$ represents the $-Val-Tyr-OR^2$ the hydroxyl group in tyrosine is susceptible to TIB and has to be protected during the amide/amine conversion step. When a compound of formula (I) is desired wherein $R^1$ is an $-OR^2$ group, and cleavage of the protecting groups is carried out before the amide/amine conversion by TIB, an intermediate of formula (VII)

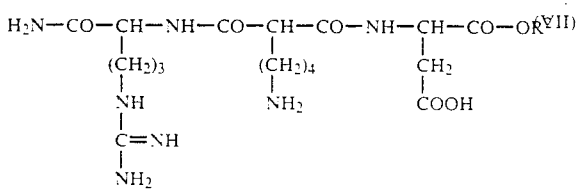

is obtained which is then reacted with TIB to afford the desired retro-inverso peptide of formula (I). A further object of the present invention are therefore the intermediates of formulas (V), (VI), and (VII) which are obtained in the synthesis of the pharmacologically active compounds of formula (I). In more detail, the first step of the process of the invention may conveniently be carried out according to any of the coupling methods known in literature for peptide synthesis.

Optimum results, in terms of yields and purity of the products, are obtained when a carbodiimide, such as dicyclohexylcarbodiimide or diisopropylcarbodiimide, and 1-hydroxybenzotriazole are employed. More particularly the reaction is carried out by adding a slight excess 1-hydroxybenzotriazole to a solution of the starting acid of formula (II), at low temperature, followed by the addition of dicyclohexyl- or diisopropyl-carbodiimide, and then of the reaction partner of formula (III).

The conventional polar aprotic organic solvents which are capable of dissolving the reactants and do not negatively interfere with the reaction course are employed for this condensation step, which is conveniently carried out at a temperature comprised between 0° C. and room temperature.

Solvents of choice are dimethylformamide, acetonitrile, and dimethylsulfoxide, optionally mixed with less polar solvents, such as for instance the halogenated aliphatic hydrocarbons, e.g. methylene chloride, dichloroethane, etc..

Protecting groups which can suitably be employed in this process are the conventional ones, known in literature and commonly employed in peptide chemistry. In particular, according to a preferred embodiment of the process of the present invention $P^L$ is a benzyloxycarbonyl group, optionally nitro-or halo-substituted; $P^G$ is a variously substituted benzenesulfonyl group such as for instance an alkylbenzenesulfonyl group e.g. toluenesulfonyl, or alkyl-alkoxy-benzenesulfonyl, e.g. 4-methoxy-2,3,6-trimethylbenzenesulfonyl; $P^I$ is preferably a tert-butyl, or tert-amyl group, as these groups proved to be stable toward TIB; and, finally, P is any of the conventional protecting groups of the terminal carboxyl function, such as, for instance, an alkyl group e.g. a tert-butyl or tert-amyl group, or an aralkyl group e.g. benzyl or substituted benzyl.

When the condensation reaction, whose course can be easily monitored by tlc, is complete, the thus obtained product is recovered by conventional techniques.

In particular, when, according to a preferred embodiment of the process of the present invention, a carbodiimide is used as the coupling agent, said techniques involve separation, by filtration, of the urea which forms, evaporation of the solvent, washing of the residue or of a solution thereof with slightly basic and slightly acidic solutions, and purification of the obtained intermediate product by crystallization or chromatography.

The reaction of the thus obtained product with TIB is then performed according to the method described in Italian patent application 25755 A/81, which involves reaction of the amide substrate with a slight excess of TIB in the presence of a mixture of water and inert organic solvents such as for instance dimethylformamide, acetonitrile, etc., as the reaction solvent. The reaction is carried out by bubbling an inert gas, typically nitrogen, through the reaction mixture and checking the reaction course by tlc. When the amide/amine conversion is complete, the organic solvent is removed and the product can be easily recovered by lyophilization. If desired, acylation of the obtained product can then be carried out using an active ester of the acid R—OH, such as for instance the p-nitro-phenyl ester, the 2,4,5-trichloro-phenyl ester, etc.. Removal of the protecting groups may be effected by methods known in the art for the respective protecting groups. In general, when conventional protecting groups are employed, such as tert-butyl or tert-amyl for the protection of the hydroxyl function in tyrosine and of carboxyl groups, tert-butoxycarbonyl or benzyloxycarbonyl for ε-amino protection in the lysine residue, and benzenesulphonyl groups for the guanidino group in arginine, these are conveniently cleaved by acidolysis in acidic medium, such as for instance diluted hydrochloric acid in acetic acid, trifluoroacetic acid or trifluoroacetic acid and trifluoromethanesulfonic acid mixtures, in the presence of small amounts of ethanedithiol, anisole, thioanisole, or resorcinol used as scavengers to trap the carbocations which form. At the end of the deprotection step, the desired compound of formula (I), as such or as a corresponding addition salt, is recovered and purified by conventional methods. When a compound of formula (I) is desired wherein R is hydrogen and $R^1$ is an $—OR^2$ group, as anticipated, the sequential arrangement of amide/amine conversion and deprotection steps is preferably reverted. The general methods for carrying out these steps are however the same.

Homogeneity of the compounds of formula (I) thus obtained is assayed by tlc and HPLC while their purity is determined by amino acid analysis and NMR spectrometry.

The starting compounds of formulas (II) and (III) can be easily prepared from commercially available products or can be easily prepared by techniques known in the field of peptide synthesis and organic chemistry.

In particular, the fragment of formula (II) is conveniently prepared starting from an amide of formula (VIII)

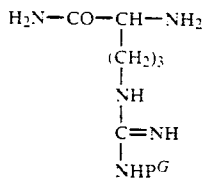

wherein $P_G$ is a protecting group of the guanidino function, and a 2-substituted malonic acid hemiester of formula (IX)

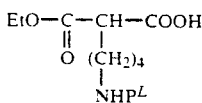

wherein $P^L$ is a suitable protecting group of the amino function, according to methods known in peptide synthesis.

In its turn, the compound of formula (VIII) is prepared from the corresponding amino acid, suitably protected at the guanidino and amino functions, by forming the amide and then deprotecting the amino group, while the compound of formula (IX) is prepared starting from diethyl malonate by the introduction of the substituent at the 2-position followed by a partial hydrolysis of the diester. The methods for preparing the peptide fragment of formula (III) are those conventionally employed in the synthesis of oligopeptides.

The compounds of the present invention may exist in two isomeric forms.

In structural formula (I) in fact there exist at least three asymmetric carbon atoms, but the terminal amino acid or acids (Asp, Val, Tyr) are of the "natural" or L-configuration (fragment (III) is prepared starting from the suitably selected L-aspartic acid, L-valine, and L-tyrosine derivatives), and the absolute configuration of the gem-diamino carbon atom is also fixed, as the fragment of formula (VIII) is obtained starting from D-arginine. Finally, the malonyl asymmetric carbon atom may have either the R- or S-configuration. Therefore the compounds of formula (I) may be obtained and used as pure isomers or as mixtures thereof in any proportions. When the process for preparing the compounds of formula (I) leads to a mixture of diastereoisomers, said mixture may however be separated, if desired, into the single diastereoisomers, according to known resolution methods.

The following examples describe in detail some representative compounds of the present invention and the process for the preparation thereof, but should in no way be interpreted as a limitation to the scope thereof.

Example 1

Synthesis of [gArg¹,(RS)mLys²]TP5 acetate (the compound of formula (I) wherein R=H;

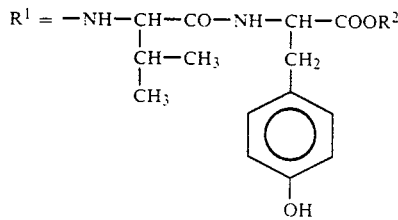

$R^2 = H$)

1) L-tyrosine-O-tert-butyl ether tert-butyl ester formate salt (H—Tyr(OBu$^t$)OBu$^t$.HCOOH)

A solution of ammonium formate (0.73 g, 11.7 mmol) in methanol (10 ml) and palladium on charcoal (1.5 g) are added to a solution of L-tyrosine-O-tert-butyl ether tert-butyl ester (Tyr(OBu$^t$)OBu$^t$) prepared according to the method described in "New Aspects in Physiological Antitumor Substances", Karger, Basel (1985), p.33, (2 g, 4.68 mmol) in methanol (20 ml). The resulting solution is kept at 25° C. for about 25 minutes. The reaction mixture is then filtered on celite and the solvent is evaporated off giving a clear oil (1.6 g, 87%). $R_f$ (CMA, 85:10:5 by volume) 0.2 (CMA=chloroform:methanol:acetic acid).

2)
Nα-(Nα-benzyloxycarbonyl-valyl)tyrosine-O-tert-butyl ether tert-butyl ester (Z-Val-Tyr(OBu$^t$)-OBu$^t$)

A solution of 1-hydroxy-benzotriazole (HOBt) (0.652 g, 4.47 mmol) in dimethylformamide (DMF) (5 ml) and a solution of dicyclohexylcarbodiimide (DCC) (0.921 g, 4.47 mmol) in DMF (5 ml) are stirred into a solution of Nα-benzyloxycarbonyl-L-valine (Z-Val) (1.12 g, 4.47 mmol) in DMF (25 ml) cooled to 0° C. About 30 minutes later, the ice bath is removed and stirring is continued for additional 30 minutes. A solution of the compound obtained in step 1) (1.19 g, 4.06 mmol) and N-methyl-morpholine (NMM) (0.41 g, 4.06 mmol) in DMF (15 ml) is then added thereto. The mixture is allowed to stand at room temperature for one hour. Dicyclohexylurea (DCU) which forms is then filtered off and the filtrate is evaporated to dryness. The obtained oil is taken up in ethyl acetate (AcOEt) (50 ml) and stirred for 20 minutes with 5% aqueous sodium bicarbonate solution. The organic phase is separated and washed sequentially with 5% sodium bicarbonate, water, 0.1N HCl, and finally with water. By evaporating off the organic solvent, a raw solid residue is obtained which is dissolved in the minimum amount of hot isopropyl ether and crystallized therefrom upon cooling. A clear crystalline product is obtained (1.6 g, 75%). M.p. 114°–5° C. and $R_f$(CMA, 85:10:5 by volume) 0.8.

(3)
Nα-(Nα-benzyloxycarbonyl)-aspartyl(β-tert-butyl)-
-valyl-tyrosine-O-tert-butyl ether tert-butyl ester
(Z—Asp(OBu$^t$)—val—Tyr(OBu$^t$)—OBu$^t$)

A solution of HOBt (0.434 g, 2.97 mmol) in DMF (3 ml) and a solution of DCC (0.613 g, 2.97 mmol) in $CH_2Cl_2$ (10 ml) are added to a solution of Nα-benzyloxycarbonyl-aspartic acid (β-tert-butyl ester) (Z-Asp(OBu$^t$)-OH) (1.06 g, 2.97 mmol) in $CH_2Cl_2$ (20 ml) cooled to 0° C. and kept under vigorous stirring.

After 30 minutes, the temperature is allowed to rise to the room value and stirring is prolonged for additional 30 minutes. A solution of HCOOH·H—Val—Tyr-(OBu$^t$)—OBu$^t$ (1.26 g, 2.7 mmol) (obtained from the intermediate prepared in step 2) by conventional removal of the benzyloxycarbonyl group by catalytic hydrogenolysis with ammonium formate and palladium) and NMM (0.207 g, 2.7 mmol) in DMF (15 ml) is added to the mixture.

The reaction mixture is stirred at room temperature for 24 hours, the DCU which forms is then removed by filtration and the solvent is evaporated off again under reduced pressure.

The residue is taken up in AcOEt (50 ml), sat. $NaHCO_3$ is added and the mixture is stirred for 20 minutes. The aqueous phase is discarded and the organic phase is washed with a sat. $NaHCO_3$, water, 0.1N HCl, and water. The organic phase is dried over $MgSO_4$ and concentrated to dryness.

The product is crystallized from ethyl acetate/hexane yielding a microcrystalline clear product (1.7 g, 90%) with m.p. 184°–85° C. and $R_f$(CMA, 85:10:5 by volume) 0.9.

4)
Nα-fluorenylmethoxycarbonyl-N$^G$-(4-methoxy-2,3,6-
-trimethyl)benzenesulphonyl-D-argininamide
(Fmoc—D—Arg(Mtr)—NH$_2$)

A solution of 1-hydroxy-benzotriazole ammonium salt (HOBt·NH$_3$) (3.0 g, 16.45 mmol) and DCC (3.38 g, 16.45 mmol) in DMF (10 ml) is added to a stirred solution of Nα-fluorenylmethoxycarbonyl-N$^G$-(4-methoxy-2,3,6-t-rimethyl)benzenesulphonyl-D-arginine (Fmoc—D—Arg(Mtr)—OH) (10 g, 16.45 mmol) in DMF (60 ml) cooled to 0° C.

After about one hour the temperature is allowed to rise to room temperature and stirring is prolonged for additional 60 minutes.

The DC which forms is then removed by filtration and washed with DMF (10 ml). The DMF washings are then added to the filtrate. By evaporating off the solvent an oily residue is obtained which is taken up in AcOEt and washed first with 5% sodium bicarbonate solution and then with saturated sodium chloride.

The organic solution is then dried over $MgSO_4$ and concentrated to dryness. The solid residue which is obtained is triturated with ethyl ether (100 ml) to afford a white solid (9.2 g, 93 % yield) with m.p. 168°–72° C.

Chromatographic analyses (tlc and HPLC) did not reveal any impurities.

(5)
N$^G$-(4-methoxy-2,3,6-trimethyl)benzenesulphonyl-D-
-argineamide hydrochloride
(HCl·H—D—Arg(Mtr)—NH$_2$)

A suspension of the compound obtained in step 4) (9 g, 15.5 mmol) in a mixture of DMF and diethylamine 80:20 (100 ml) is stirred for one hour. The solvent is then evaporated off under reduced pressure and the residue is taken up in AcOEt (100 ml) and extracted with diluted hydrochloric acid (50 ml × 3). The aqueous extracts are pooled, washed with additional AcOE and repeatedly lyophilized yielding an uncolored flaked product (4.5 g, 80% yield). This product does not show a clearly discernible melting point. Chromatographic analysis does not reveal any impurities.

6) 2-(N-tert-butoxycarbonyl-4-butylamino)malonic acid diethyl ester (OEt—mLys(Boc)—OEt)

Metallic sodium (0.28 g, 0.012 mol) is dissolved in absolute ethyl alcohol (EtOH) (9 ml) under nitrogen atmosphere. The mixture is heated to 60° C. and diethyl malonate (3.8 g, 0.024 mol) is then dripped therein. N-tert-butoxycarbonyl-4-chloro-butylamine (2.5 g, 0.012 mol) is then gradually added, at room temperature, to the resulting solution. The reaction mixture is stirred at room temperature for 2 hours and at the reflux temperature for 6 hours, and then poured into a mixture AcOEt/water (100 ml 1/1 v/v). The organic phase which is separated is then washed repeatedly with water and dried over $MgSO_4$ The solvent is removed under vacuum at 100° C. affording a crude oily product which is purified by reverse-phase HPLC on an RP-18 column eluting with an aqueous phase modified with $CH_3CN$ (45% by volume). The desired compound (1.31 g) is thus obtained as a pure product.

(7) 2-(N-tert-butoxycarbonyl-4-butylamino)malonic acid ethyl hemiester (HO—(R,S)mLys(Boc)—OEt)

A solution of KOH (9.97 mmol) in EtOH (10 ml) is added dropwise to a suspension of the compound obtained in the preceding step (3.48 g, 10.5 mmol) in EtOH (15 ml).

After 16 hours the reaction mixture is taken up in water and extracted with ethyl ether. The aqueous phase is then acidified with 1N HCl up to pH 3 and extracted again with AcOEt. The organic extracts are combined, washed with saturated sodium chloride and dried over $MgSO_4$.

By evaporating off the solvent under reduced pressure the desired product is obtained as a clear oil. HPLC analysis did not reveal any impurities while the NMR spectrum confirmed the assigned structure.

(8)
(R,S)-malonyl-2-(N-tert-butoxycarbonyl)-4-butylamine-$N^G$-(4-methoxy-2,3,6-trimethylbenzenesulfonyl)--D-arginineamide ethyl ester
($H_2N$—D—Arg(Mtr)—(R,S)mLys(Boc)—OEt)

A solution of HOBt (0.159 g, 1.1 mmol) in DMF (3 ml) and a solution of DCC (0.204 g, 1.0 mmol) in DMF (5 ml) are added to a solution of the compound of the preceding step (0.30 g, 1.0 mmol) in DMF (10 ml) cooled to 0° C. and kept under vigorous stirring. One hour later, the temperature is allowed to increase to the room value and stirring is prolonged for additional 60 minutes. A solution of the compound obtained in step 5) (0.502 g, 1.2 mmol) and NMM (1.120 g, 1.2 mmol) in DMF (10 ml) is then added thereto. After 4 hours, having checked the disappearance of HO—mLys(Boc)—OEt by tlc, the reaction mixture is filtered and the filtrate is brought to dryness. The residue which is thus obtained is taken up in AcOEt and the organic solution is washed sequentially with 5% sodium bicarbonate, water, 0.1 N HCl, and water. The organic solution is dried over $MgSO_4$ and evaporated. The oily residue which is obtained is triturated with hexane, finally yielding a finely divided white powder (0.546 g, 68% yield). M.p. 147°–49° C. (dec.). Chromatographic analyses (tlc and HPLC) did not reveal any impurities while the NMR analysis confirmed the assigned structure.

(9)
N-(R,S)malonyl-2-((N-butoxycarbonyl)-4-butylamine)--$N^G$-(4-methoxy-2,3,6-trimethylbenzenesulfonyl)--D-arginineamide
($H_2N$-D-Arg(Mtr)-(R,S)mLys(Boc)-OH)

A solution of KOH (0.017 mg, 0.30 μmol) in EtOH (1 ml) is added dropwise, within 2 hours, to a solution of the compound of the preceding step (180 mg, 0.26 mmol) in EtOH (8 ml) cooled to 0° C., and the reaction mixture is then stirred for 16 hours. The mixture is then diluted with water and brought to a small volume by evaporation under reduced pressure. It is then extracted with ethyl ether (3×50 ml), the aqueous phase is acidified by the addition of 0.1N HCl up to pH 3 and extracted again with AcOEt. The organic extracts are combined, dried over $MgSO_4$ and evaporated. The oily residue is triturated with ethyl ether affording the desired compound (0.160 g, 85% yield) as a chromatographically (tlc and HPLC) pure product. The NMR analysis confirmed the assigned structure.

(10)
Nα-(R,S)-malonyl-2-((N-tert-butoxycarbonyl)-4-aminobutyl)-aspartyl(β-tert-butyl ester)valyl-tyrosyl(O-tert-butyl ether) tert-butyl ester-$N^G$-(4-methoxy-2,3,6-trimethylbenzenesulfonyl)-D-arginineamide
($H_2N$—D—Arg(Mtr)—(R,S)mLys(Boc)—Asp(OBu$^t$)—Val—Tyr(—OBu$^t$)—OBu$^t$).

A solution of HOBt (39 mg, 0.26 mmol) and DCC (55 mg, 0.26 mmol) in DMF (4 ml) is added to a solution of the compound obtained in the preceding step (170 mg, 0.26 mmol) in DMF (8 ml) cooled to 0° C. After 60 minutes the temperature is allowed to rise to room temperature and stirring is continued for additional 60 minutes. Nα-aspartyl(β-tert-butyl ester)valyl-tyrosyl-O-tert-butyl ether tert-butyl ester (H—Asp(OBu$^t$)—Val—Tyr(OBu$^t$)—OBu$^t$) (243 mg, 0.39 mmol) (obtained from the compound prepared in step 3) by cleavage of the benzyloxycarbonyl group through catalytic hydrogenolysis with ammonium formate and palladium), and NMM (39 mg, 0.39 mmol) are then added to the above solution. After 16 hours the DCU is removed by filtration and the filtrate is concentrated to dryness. The solid residue which is obtained is triturated with hexane affording a finely divided white powder. The usual washings with basic (5% sodium bicarbonate) and acid (0.1 N HCl) solutions are then carried out by suspending the obtained product into the washing solutions. The desired product (250 mg, 72% yield) is thus obtained.

11) [gArg1,(RS)mLys²]TP5 acetate
(AcOH·H—gArg—(R,S)mLys—Asp—Val—Tyr—OH)

The compound of the foregoing step (300 mg) is dissolved into a mixture of $CH_3CN$ and $H_2O$ (8 ml of $CH_3CN$ and 10 ml of $H_2O$). A solution of TIB (120 mg) in $CH_3CN$ (2 ml) is then added thereto under nitrogen atmosphere and the resulting mixture is stirred for 3 hours.

The reaction mixture is then brought to dryness giving a yellowish oil. Amino acid analysis confirmed that the arginineamide had been converted into a gem-diamino group.

The obtained crude oil (150 ml) is taken up in a mixture of ethanedithiol, trifluoroacetic acid, and trifluoromethanesulfonic acid (10:89:1) (100 ml) and is allowed to react for about 20 minutes. Triethylamine (1.5 ml) is added to the resulting mixture which is then brought to dryness under a nitrogen stream.

The residue is partitioned between ethyl ether and water. The organic phase is separated and extracted thoroughly with water. The aqueous phases are combined, extracted with ethyl ether following the disappearance of ethanedithiol and then repeatedly lyophilized. The product is isolated as the acetic acid addition salt by ion exchange chromatography on a CM-Sephadex G-25 column (15×0.9 cm; 2 g) and eluted with a linear gradient ammonium acetate from 0.1 to 0.6M, pH 4.4, with a flow rate of 42 ml/min. Those fractions which contain the desired product are pooled, concentrated to a small volume under reduced pressure and lyophilized. 45 Mg of a solid (yield : 42% of the theory) is obtained. Chromatographic and NMR analyses confirmed the purity of the compound and its structure.

Example 2

Synthesis of [gArg¹,(R.S)mLys²]TP5$^{1-3}$ acetate
(AcOH·H—gArg—(R,S)mLys—Asp—OH)

(1)
Nα-(R,S)-malonyl-2-((N-tert-butoxycarbonyl)-4-aminobutyl)-aspartyl-(α, β-tert-butyl ester)-$N^G$-(4-methoxy-2,3,6-trimethylbenzenesulfonyl)-D-arginineamide ($H_2N$—D—Arg(Mtr)—(R,S)mLys(Boc)—Asp(OBu$^t$)—OBu$^t$)

A solution of HOBt (28 mg, 0.20 mmol) and DCC (40 mg, 0.20 mmol) in DMF (5 ml) is added to a solution of the compound obtained in step 9) of Example 1 (130 mg, 0.20 mmol) in DMF (5 ml) cooled to 0° C. and kept under stirring. After 60 minutes the mixture is allowed to reach room temperature and stirring is prolonged for additional 60 minutes. A solution of NMM (21 mg, 0.21 mmol) and H-Asp(OBu$^t$)-OBu$^t$ (39 mg, 0.21 mmol) in DMF (3 ml) is then added thereto. After 16 hours the reaction is blocked by removing the solvent. The obtained residue is then taken up in AcOEt and filtered. A saturated sodium bicarbonate solution is added to the filtrate and the mixture is stirred for 30 minutes. The organic phase is separated, washed consecutively with a saturated sodium bicarbonate solution, water, 0.1N HCl, and water, and it is dried over MgSO$_4$. The residue which is obtained by evaporating off the solvent is then crystallized from AcOEt/hexane yielding the desired product (140 mg) with m.p. 156°-58° C. and $R_f$ (CMA, 85:10:5 by volume) 0.4.

(2) [gArg$^1$,(R,S)mLys$^2$]TP5$^{1-3}$ acetate (AcOH.H-gArg-(R,S)mLys-Asp-OH)

The compound of the foregoing step (50 mg) is dissolved into a mixture of ethanedithiol, trifluoroacetic acid, and trifluoromethanesulfonic acid (10:89:1) (20 ml) under nitrogen atmosphere. After 15 minutes the mixture is cooled to 0° C. and triethylamine (0.3 ml) is added. The mixture is evaporated to dryness under a nitrogen stream, the obtained residue is taken up in water (25 ml) and extracted with ethyl ether (10 ml). The separated organic phase is extracted with water (25 ml) and then discarded. The aqueous extracts are combined, washed with ethyl ether (2×10 ml) and lyophilized affording a white solid (25 mg).

$R_f$ (BPAW, 15:3:12:10 by volume, upper phase) 0.2 (single spot)

(BPAW=butanol:pyridine:acetic acid:water)

I,I-bis-(trifluoroacetoxy)iodobenzene (36 mg) is added to a solution of the above product in CH$_3$CN/H$_2$O(50/50, v/v) (6 ml) and the reaction mixture is stirred for 4 hours and brought to dryness. The residue is taken up in H$_2$O (50 ml) and washed with ethyl ether (3×25 ml). The aqueous phase is then diluted and lyophilized. The product of the title is isolated by ion exchange chromatography on a CM-Sephadex G-25 column (15×0.9 cm; 2 g) and eluted with a linear gradient ammonium acetate, pH 4.4, from 0.15 to 0.6M in 8 hours, with a flow rate of 42 ml/min.

Fractions are collected every 6 minutes.

Those fractions which contain the desired product are combined, concentrated to a small volume under reduced pressure and lyophilized. The compound of the title (12 mg) is thus obtained as a white solid (yield 43%). Chromatographic ($R_f$ (BPAW) 0.15) and NMR analyses confirmed the purity of the product and the assigned structure.

We claim:

1. A compound of formula (I)

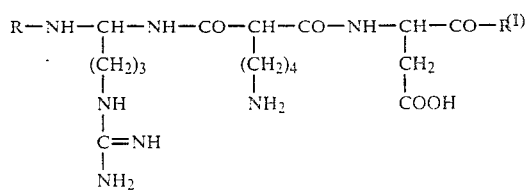

wherein

R is hydrogen or an acyl radical, and

R$^1$ is an —OR$^2$ wherein

R$^2$ is hydrogen or a straight or branched alkyl radical of from 1 to 6 carbon atoms, a straight or branched alkenyl or alkynyl radical of from 3 to 6 carbon atoms, or an aryl-alkyl or alkyl-aryl radical of from 7 to 12 carbon atoms, and the corresponding pharmaceutically acceptable acid- or base-addition salts.

2. A compound of claim 1 wherein R is hydrogen and R$^1$ is an —OR$^2$ wherein

R$^2$ is a hydrogen atom.

3. A compound of claim 2 wherein R$^1$ is a group —OR$^2$.

4. A compound of claim 3 selected from [gArg$^1$,(R,S)mLys$^2$]TP5$^{(1-3)}$ and the addition salts thereof.

5. A pharmceutical composition containing a pharmaceutically acceptable carrier and an immunoregulating amount of a compound of claim 1 as the active principle.

* * * * *